United States Patent [19]

Vassarotti et al.

[11] Patent Number: 5,167,810
[45] Date of Patent: Dec. 1, 1992

[54] END CELL FOR CHROMATOGRAPHY COLUMN

[75] Inventors: Vincenzo Vassarotti, Bugnaux-sur-Rolle, Switzerland; Colin K. Lanyi, Stroud; Christopher R. Biddell, Stonehouse, both of England

[73] Assignee: Amicon Ltd., Gloucestershire, England

[21] Appl. No.: 758,935

[22] Filed: Sep. 11, 1991

[30] Foreign Application Priority Data

Sep. 19, 1990 [GB] United Kingdom ............... 9020449

[51] Int. Cl.⁵ ................................ B01D 15/08
[52] U.S. Cl. .................... 210/198.2; 210/656; 55/386; 264/257; 264/324; 264/DIG. 67
[58] Field of Search ............ 264/257, 324, DIG. 67; 210/656, 198.2, 238, 241, 246, 445, 446, 450, 495, 496; 422/70; 55/386

[56] References Cited

U.S. PATENT DOCUMENTS

| | | | |
|---|---|---|---|
| 2,015,426 | 9/1935 | Gough | 264/324 |
| 2,417,510 | 3/1947 | McGinnis | 264/324 |
| 3,487,938 | 1/1970 | Patterson | 210/198.2 |
| 4,361,482 | 11/1982 | Teetz | 210/198.2 |
| 4,643,863 | 2/1987 | Martini | 264/DIG. 67 |
| 4,769,141 | 9/1988 | Couillard | 210/198.2 |
| 4,865,728 | 9/1989 | Larsson | 210/198.2 |
| 4,888,112 | 12/1989 | Kronwald | 210/450 |
| 4,927,531 | 5/1990 | Sakamoto | 210/198.2 |

FOREIGN PATENT DOCUMENTS

| | | | |
|---|---|---|---|
| 0008921 | 8/1979 | European Pat. Off. | 210/198.2 |
| 1149852 | 4/1966 | United Kingdom | 210/198.2 |
| 1148662 | 5/1966 | United Kingdom | 210/198.2 |

OTHER PUBLICATIONS

Abstract of Swedish Patent No. 459396 published Jul. 3, 1992.

Primary Examiner—Ernest G. Therkorn
Attorney, Agent, or Firm—Margit Maus; William L. Baker

[57] ABSTRACT

An end cell for a chromatography column has a moulded plastics structure and an integral screen formed of a woven mesh of fibres of the same plastic material as used for the end cell. A peripheral ring of the same plastics material is injection moulded to the perimeter of the mesh, said ring being secured to the end cell in a leak-proof manner, preferably by ultrasonic welding.

9 Claims, 2 Drawing Sheets

END CELL FOR CHROMATOGRAPHY COLUMN

The present invention relates to an end cell for a chromatography column, and in particular to the provision of a screen therefor which can pass liquid to be separated into the bed at one end, while a similar screen can pass the liquid from the bed at the other end; these screens maintain the chromatography media of the bed in the column contained to one side of the screen.

Chromatography columns are used for both laboratory analysis operations and for factory scale production operations in which separation steps such as separating out a fraction from human blood or separating out impurities from a pharmaceutical can be carried out on a large scale in a batch process.

In all these cases there is a need for a screen to contain the chromatography bed in the column and to define with the end cell a plenum chamber throughout which the liquid to be separated can be distributed evenly before passing through the column by permeation inwardly at one end (usually the upper end) and permeation outwardly through a similar screen (usually at the bottom end) as the leading fraction of the separated material reaches the delivery end of the bed. The provision of such a screen at the bottom end of the column also enables the chromatography column to be used with an upward flow of liquid to be separated.

The development of chromatography columns has aimed at providing ease of operation and various additional benefits which have particular commercial importance. These include : (a) the ability to be sterilized by autoclaving (b) improved sanitation by virtue of design features giving less carryover of product from one batch to the next, (c) the ability to resist solvents which may be used in the material to be separated, (d) conformity to food grade FDA regulations, (e) an improved pressure tolerance, and (f) lower cost.

As will be appreciated from the above, the material used for this screen should be inert to the materials being separated, and should preferably also be resistant to solvents. As a still more preferable characteristic the material should be autoclaveable (i.e. heat-sterilizable), although in practice severe contamination of a chromatography end cell will best be dealt with by disposal of that end cell and replacement by a new one.

In order to provide best solvent tolerance, as many as possible of the components used in the manufacture of a chromatography column are of the same material which is one chosen for its resistance to the materials being separated, and for its ability to withstand the effects of high pressure and high temperature during operation and during sterilization.

Such inert end cells have in the past been made of several different components which are all assembled by the user and which may be replaced individually in the event of damage or contamination of one of these components of the end cells.

In addition to sintered stainless steel or woven stainless meshes, chromatography columns on both laboratory and process scale have used both sintered plastic materials, usually polyethylene or polytetrafluoroethylene (PTFE) with nominal porosities of 30 $\mu$m or 10 $\mu$m (in the case of small PTFE discs) and woven plastic meshes usually nylon (polyamide) again with porosities of 30 or 10 $\mu$m. Usually these woven meshes have been single weave materials.

Accordingly, the present invention provides an end cell for a chromatography column, comprising : an end cell body; a woven mesh screen for isolating the end cell from a chromatography bed, in use; and a peripheral ring cast on the perimeter of the mesh screen and sealingly secured to the end cell, wherein a common material is used for the end cell, the screen, and the ring.

BRIEF DESCRIPTION OF THE DRAWING

In order that the present invention may more readily be understood the following description is given, merely by way of example, with reference to the accompanying drawings, in which.

DESCRIPTION OF THE PREFERRED EMBODIMENTS

Figure 1:
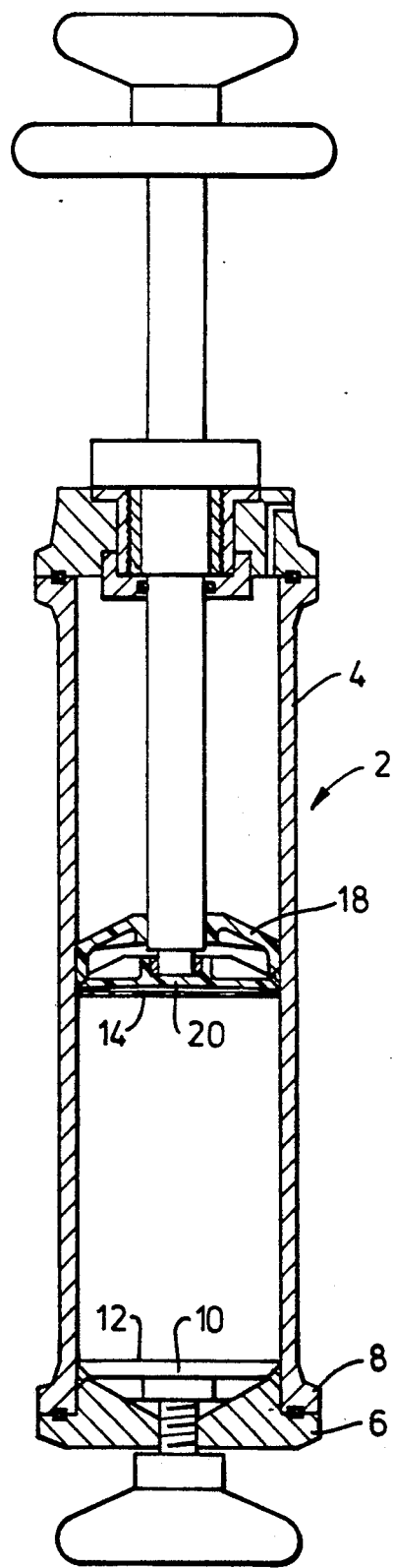
FIG. 1 is a longitudinal sectional view of a chromatography column in accordance with the present invention.

FIG. 1 shows a chromatography column 2 comprising a column tube 4 having at its lower end an end cap 6 clamped to a lower flange 8 by means of a suitable clamp (not shown). The lower end cap 8 includes a moulded, preferably plastic, end cell component 10 including a liquid-permeable screen 12.

The bed of absorption media of the chromatography column is disposed between the screen 12 and a similar screen 14 of a piston 18 which again includes a moulded plastic end cell component 20 supporting the upper screen 14.

We have found that it is advantageous to manufacture the end cell components from the same material as the screens, and we prefer to use a plastic material for the screen and end cell.

Generally any solvent-resistant plastic material which is also resistant to temperatures of well in excess of 100° C., for example up to 200° C., is suitable for the end cell. The preferred material at the present time is polymethyl pentene (available from the Mitsui Petrochemical Company of Japan under the Trade Mark TPX) which has the additional advantage of being transparent so as to allow its use for the column tube 4. Other possible such materials include polypropylene, polysulphone and glass reinforced polyester.

However, we find that when a mesh of plastic fibres is to be used as the screen, in conjunction with an end cell of the same plastic material, there are problems arising as a result of the ragged ends of the fibres at the perimeter of the disc of the mesh. Furthermore, it is difficult to bond the fibres to the body of the end cell in a reliable manner and without the generation of gaps through which liquid may pass more rapidly than at other points on the surface of the screen.

It will be appreciated that in order to preserve uniformity of flow of the liquid being separated through the bed there is a need for accurate distribution of the flow of the liquid over the upper surface of the screen 14 of the upper end cell 20, and likewise in order to allow for uniformity of flow approaching the screen 12 of the lower end cell 10 a similar uniformity of pore size must be provided for.

Figure 2:
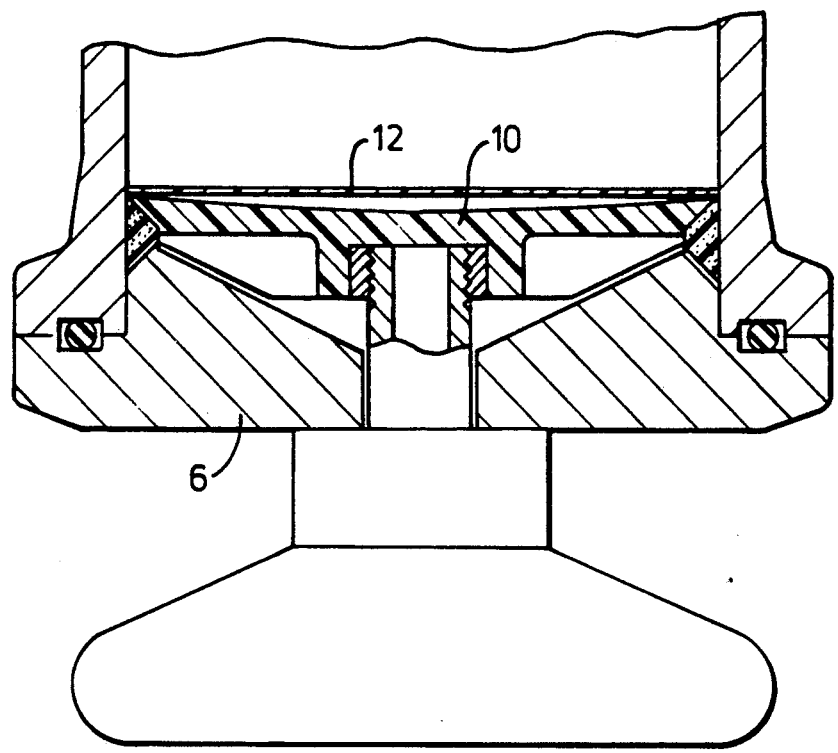
FIG. 2 is a detail of the lower end cell of the column of FIG. 1.
Figure 3:
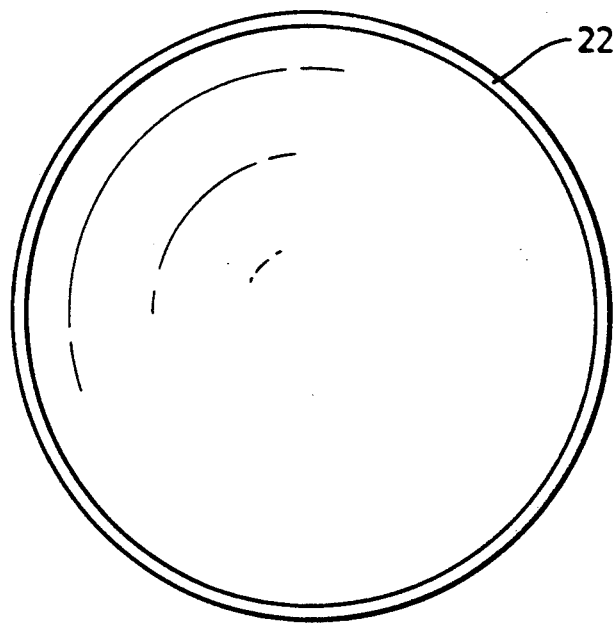
FIG. 3 is a plan view of the screen of the end cell of FIG. 2, before insertion in the end cell body.

FIG. 2 shows in detail the end cell structure at the lower end cap 6. The lower end cell 10 which, as described above, is preferably of moulded plastic construction and is for example formed by injection moulding of polymethyl pentene or polypropylene or polysulphone. If desired, the structure may include glass fibre reinforcement.

The upper surface of the end cell 10, i.e. the surface adjacent the screen 12, is upwardly concave in a flat frusto-conical form and includes distribution ribs (not shown) which help to direct the flow of liquid being separated across the whole extent of the screen for substantially uniform pressure and flow rates through the screen at all points over its area. Also omitted from the drawing is a passage through the end cell 8 to allow the liquid leaving the bottom of the bed via the screen 12 to be collected as product.

In practice, the product will be equivalent to the starting material less one or more of its constituents which will have been retained on the bed and which can be recovered from the bed, for example by subsequent washing of the bed media. In some cases it is the retained constituent which is the product; in other cases the purified starting medium less the retained constituent is to be the product.

The method of forming the screen and of securing it in place is the same for the lower screen 12 as for the upper screen 14, and therefore the description which follows will be based on the structure of the lower end cell screen 14 shown in FIG. 2.

Fibres of the chosen material, e.g. polypropylene or polymethyl pentene are woven into a double mesh having a coarse layer and a fine layer with the pore size on the fine layer of the desired range for fine separation.

Next the mesh is cut into discs having a diameter substantially that required for the end cell screen 12 of FIG. 2. In order to prepare the disc for mounting in the end cell 10 of FIG. 2, a peripheral ring 22 is then injection moulded on the perimeter of the disc, this ring preferably being formed of the same plastic material as the mesh and having a contour which will readily conform to the contour of the end cell 10 to which the disc is to be bonded.

The bonding operation involves welding, for example ultrasonic welding, of the ring 22 to the end face of the end cell 10 on the dished side, and can be achieved such that there is no leakage path between the end cell and the mesh, and such that all liquid entering the bed at the upper screen 14 or leaving the bed at the lower screen 12 must pass through the body of the woven mesh.

Advantageously the column tube is itself formed of the same plastic material as the mesh (e.g. polypropylene, polysulphone, glass reinforced polyester or polymethyl pentene), and so also are the lower end cap 6, the upper end cap, and the remainder of the piston 18 apart from the seal. Particularly in the case of polymethyl pentene, this will give rise to a transparent chromatography column having adequate mechanical strength, and the ability to be heat-sterilized thereby enabling the use of autoclaves.

Polymethyl pentene has the advantage that in the event of over-pressure within the column 2 the column tube 4 will rupture or split rather than shattering.

The operation of bonding the screen 12 to the end cell 10 is effected during manufacture of the end cell, in order to ensure high leak-proof quality of the end cell/screen combination. As a result, when a screen becomes contaminated, it is necessary to replace the entire end cell rather than removing that screen from one end cell (which might entail damage of the end cell and the temptation to re-use the end cell with adverse consequences in terms of product contamination) and then replacement of that screen by a new one.

The use of a composite woven mesh gives the following advantages:

(i) It is much easier to obtain uniform permeability with a mesh than with a sintered material.

(ii) A composite mesh (that is one with a fine front mesh of 5 $\mu$m to 50 $\mu$m, preferably 10 $\mu$m to 30 $\mu$m to retain bed particles backed by a more open mesh for mechanical strength) is mechanically better than a single woven mesh and is easier to fix to the end cell with ultrasonic welding.

(iii) A mesh will allow air to pass through completely during the packing and the "wet out" operations. In contrast plastic sinters are hydrophobic and require prewetting with for instance alcohol and then will not allow air to pass through. This means the piston seal would need to be completely relaxed to allow the air to pass which then results in the packing slurry also passing the seal, which is undesirable.

(iv) The new design allows bonding of the bed support to the end cell to give an integral unit which facilitates cleanliness and sterility, provides maximum flow distribution area, and gives rise to no hold up volumes (dead spaces), and to no leakage around the cell periphery which would cause non-uniform flow.

The seal used for the piston 18 is able to be released and tightened from outside the column, by use of a mechanism described and claimed in our co-pending British Patent Application No. 9020450.4.

We claim:

1. An end cell for a chromatography column, comprising: a chromatography column containing an end cell body; a woven mesh screen having a perimeter for isolating the end cell from a chromatography bed, in use; and a peripheral ring cast on the perimeter of the mesh screen and sealingly secured to the end cell, wherein a common material is used for the end cell, the screen, and the ring.

2. An end cell according to claim 1, wherein said ring is fastened to the end cell by welding.

3. An end cell according to claim 2, wherein the ring is welded to the end cell by ultrasonic welding.

4. An end cell according to claim 1, wherein the end cell is formed of injection moulded plastic material, and said ring is injection moulded on to the perimeter of the mesh.

5. An end cell according to claim 1, wherein said end cell body is formed of glass reinforced plastics material.

6. An end cell according to claim 1, wherein the common material used for the woven mesh, the ring and the end cell is polymethyl pentene.

7. An end cell according to claim 1, wherein the common material used for the woven mesh, the ring and the end cell is polypropylene.

8. An end cell according to claim 1, wherein the common material used for the woven mesh, the ring and the end cell is polysulphone.

9. An end cell according to claim 1, wherein the mesh is a double weave comprising a coarse weave as support layer and a fine weave as effective mesh.

* * * * *